(12) United States Patent
Kato et al.

(10) Patent No.: US 8,642,501 B2
(45) Date of Patent: Feb. 4, 2014

(54) COMPOSITE OXIDE CATALYST

(75) Inventors: Takaaki Kato, Tokyo (JP); Satoshi Fukushima, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 1057 days.

(21) Appl. No.: 11/659,335

(22) PCT Filed: Aug. 15, 2005

(86) PCT No.: PCT/JP2005/014919
§ 371 (c)(1),
(2), (4) Date: Feb. 5, 2007

(87) PCT Pub. No.: WO2006/019078
PCT Pub. Date: Feb. 23, 2006

(65) Prior Publication Data
US 2008/0108843 A1    May 8, 2008

(30) Foreign Application Priority Data

Aug. 17, 2004 (JP) .............................. P. 2004-236956
Aug. 17, 2004 (JP) .............................. P. 2004-236957

(51) Int. Cl.
*B01J 21/08* (2006.01)
*C07C 253/00* (2006.01)
(52) U.S. Cl.
USPC ........................................ 502/248; 558/303
(58) Field of Classification Search
USPC ........................................ 502/248; 558/303
See application file for complete search history.

(56) References Cited

U.S. PATENT DOCUMENTS

| 3,736,354 A | 5/1973 | Yanagita et al. |
| 6,043,186 A | 3/2000 | Komada et al. |
| 6,143,690 A | 11/2000 | Komada et al. |

FOREIGN PATENT DOCUMENTS

| JP | 06-228074 A | 8/1994 | | |
|---|---|---|---|---|
| JP | 09-157241 A | 6/1997 | | |
| JP | 10-028862 A | 2/1998 | | |
| JP | 11-114426 A | 4/1999 | | |
| JP | 11-169716 A | 6/1999 | | |
| JP | 11-244702 A | 9/1999 | | |
| JP | 2000-2293 | * | 7/2000 | ............... B01J 27/57 |
| JP | 2000-202293 A | 7/2000 | | |
| JP | 2002-292284 A | 10/2002 | | |
| JP | 2002-301373 A | 10/2002 | | |
| JP | 2002-316052 | * | 10/2002 | ............... B01J 27/057 |
| JP | 2002-316052 A | 10/2002 | | |
| JP | 2003-316052 A | 10/2002 | | |

OTHER PUBLICATIONS

Botella et al. "Selective oxidation of propane to acrylic acid on MoVNbTe mixed oxides catalysts prepared by hydrothermal synthesis" Catalysis Letters, 2001, vol. 74, No. 3-4, pp. 149-154.*
Kuang et al. "Ultrafine La-Mo and Ce-Mo complex oxide particle catalysts for selective oxidation of toluene" Journal of Materials Chemistry 1998, vol. 8, pp. 19-20.*

\* cited by examiner

*Primary Examiner* — Joseph Kosack
(74) *Attorney, Agent, or Firm* — Birch, Stewart, Kolasch & Birch, LLP

(57) ABSTRACT

Disclosed is a complex oxide catalyst composed of catalyst particles containing Mo, V, a component X and a silica-containing carrier. The component X is at least one element selected from alkaline earth metal elements and rare earth elements. The complex oxide catalyst is supported by the carrier, and the component X is uniformly distributed in the catalyst particles.

10 Claims, No Drawings

COMPOSITE OXIDE CATALYST

FIELD OF THE INVENTION

The present invention relates to a composite oxide catalyst for use in a vapor-phase catalytic oxidation or a vapor-phase catalytic ammoxidation reaction of propane or isobutane, and a method for producing an unsaturated acid or an unsaturated nitrile by using the composite oxide catalyst.

BACKGROUND ART

Heretofore, a method for producing a corresponding unsaturated carboxylic acid or unsaturated nitrile by subjecting propylene or isobutylene to a vapor-phase catalytic oxidation or a vapor-phase catalytic ammoxidation has well been known. However, in recent years, a method for producing a corresponding unsaturated carboxylic acid or unsaturated nitrile by subjecting propane or isobutane in place of propylene or isobutene to a vapor-phase catalytic oxidation or vapor-phase catalytic ammoxidation reaction has attracted people's attention, and various types of oxide catalysts have been proposed. For example, oxide catalysts containing Mo—V—Nb—(Sb/Te) are disclosed in Patent Documents 1 and 2.

Further, examples in which a further enhancement of a catalyst performance has been achieved by adding a rare earth element or the like to the catalyst containing Mo and V are disclosed in Patent Documents 1, and 3 to 6.

Namely, when the corresponding unsaturated carboxylic acid or unsaturated nitrile is produced by subjecting propane or isobutane to a vapor-phase catalytic oxidation or a vapor-phase catalytic ammoxidation, the catalyst in which a rare earth element or the like is added to the oxide catalyst containing Mo—V is effective and many studies have so far been conducted on such catalysts as described above.

When the oxide catalyst containing Mo—V which has been added with a component of the rare earth element or the like as disclosed in Patent Documents 1, 3, 5 and 6 is used in the vapor-phase catalytic oxidation or the vapor-phase catalytic ammoxidation reaction of propane or isobutane, a yield of an object is not yet sufficient. Particularly, a carried catalyst favorable for a fluidized bed reaction tends to reduce the yield of the object. As for a reason for insufficient reaction performance, as disclosed in Patent Document 6, it is known that an addition component such as the rare earth element causes a unfavorable interaction with other metallic components in a process of preparing a slurry.

For example, there is a teaching in Patent Documents 1, 3, 5 and 6 to the effect that, when waster-insoluble solids having a relatively large average particle diameter are used, the unfavorable interaction to be generated in the process property of the slurry is reduced, to thereby enhance the yield of the object. However, in the above-described Patent Documents, not only there is no description about a uniform dispersion property of the addition component to the catalyst component at all, but also, since the solid raw material in use is not soluble in water, at the time of producing an industrial catalyst, there is a risk of clogging a pipe. Further, when an excess amount of the rare earth element or the like is added, an oxide particle made of the addition component is exposed on a surface of the catalyst and, then, a decomposition reaction of the object is promoted, to thereby reduce the yield.

In Patent Document 4, an impregnation method in which a desired element in a state of liquid is added to a catalyst which has been calcined is described. However, on this occasion, there is a problem in that, since the addition component is distributed merely on a surface of a catalyst particle and a surface of a pore, not only uniformity inside the particle is inferior, but also since it becomes necessary to calcine the catalyst again after being subjected to an impregnation operation, the operation is considered to be complicated and, also, since other metallic components are eluted in an impregnation solution, there is a risk of deteriorating the reaction performance and the like.

On the other hand, in the industrial catalyst, it is important to maintain a reaction performance not only at an initial stage, but also after a long period of use. A method in which a deteriorated catalyst is taken out and a new catalyst is replenished is considered. However, there is a problem in that such procedures as described above are time-consuming, a continuous operation is hindered and, also, it is economically not advantageous. Further, another method in which the deteriorated catalyst is taken out and regenerated and, then, replenished is considered. However, there is a problem in that such regeneration as described above is time-consuming, requires a complicated apparatuses and is not sufficiently performed. For this account, a catalyst which is small in reduction of the yield is required. For example, in Patent Document 2, an example of a catalyst in which an Mo—V—Nb—Te catalyst is subjected to a vapor-phase catalytic ammoxidation reaction of propane for 1300 hours while nearly maintaining a yield of acrylonitrile all the way is disclosed. However, an evaluation on the reaction in the above Document is made on that for such a relatively short period of time as 1300 hours and does not fully satisfy a performance necessary for an industrial application. Further, in regard to the catalyst containing Mo—V which has been added with the rare earth element or the like, there is no description on a performance of a long-term reaction at all.

Patent Document 1: JP 9-157241 A
Patent Document 2: JP 11-169716 A
Patent Document 3: JP 6-228074 A
Patent Document 4: JP 10-28862 A
Patent Document 5: JP 2000-202293 A
Patent Document 6: JP 2002-301373 A

DISCLOSURE OF THE INVENTION

Problems to be Resolved by the Invention

It is an object of the present invention to provide a composite oxide catalyst containing at least Mo, V and a component X (the component X being at least one element selected from among alkaline earth metal elements and rare earth elements) for use in production of an unsaturated acid or unsaturated nitrile, wherein the composite oxide catalyst is a novel composite oxide catalyst in which the component X is uniformly distributed inside a catalyst particle and selectivity of an object is high. It is another object of the present invention to provide a method for producing a corresponding unsaturated acid or unsaturated nitrile by subjecting propane or isobutane to a vapor-phase catalytic oxidation or a vapor-phase catalytic ammoxidation reaction by using the composite oxide catalyst.

Means of Solving the Problems

The present inventors have made eager investigation to examine the problem. As a result, it has been found that the foregoing objects can be achieved by the following composite oxide catalyst, method for producing an unsaturated acid or an unsaturated nitrile, and method for producing a composite oxide catalyst. The objects of the present invention are accomplished by a composite oxide catalyst, a method for producing an unsaturated acid or an unsaturated nitrile and a method for producing the composite oxide catalyst as described below.

(1) A composite oxide catalyst comprising a catalyst particle including Mo, V, a component X and a carrier containing silica, wherein the component X is at least one element selected from alkaline earth metal elements and rare earth elements, wherein the composite oxide catalyst is carried by the carrier, and wherein the component X is uniformly distributed in the catalyst particle.

(2) The composite oxide catalyst according to item (1), wherein a dispersion value $D_X$ of a signal intensity ratio of the component X to Si, at the time of composition analysis of a cross-section of the catalyst particle, is $0<D_X<0.5$.

(3) The composite oxide catalyst according to item (1) or (2), which further comprises a component Y, wherein the component Y is at least one element selected from Te and Sb.

(4) The composite oxide catalyst according to any one of items (1) to (3), which further comprises Nb.

(5) The composite oxide catalyst according to any one of items (1) to (4), wherein the component X is at least one element selected from Sc, Y (yttrium), La, Ce, Pr and Yb.

(6) The composite oxide catalyst according to any one of items (1) to (5), wherein the composite oxide catalyst is carried by 20 to 60% by weight of silica as $SiO_2$ equivalent.

(7) The composite oxide catalyst according to any one of items (1) to (6), wherein the composite oxide catalyst is used in a vapor-phase catalytic oxidation reaction or a vapor-phase catalytic ammoxidation reaction of propane or isobutane.

(8) A method for producing an unsaturated acid or an unsaturated nitrile, comprising using the composite oxide catalyst according to any one of items (1) to (7).

(9) A method for producing the composite oxide catalyst according to any one of items (1) to (7), comprising: mixing a silica into a mixture containing an Mo compound, a V compound and an X compound to prepare a raw material mixture; spray-drying the raw material mixture to prepare a dry powder; and calcining the dry powder.

Effect of the Invention

According to the present invention, the novel composite oxide catalyst in which the component X is uniformly distributed inside a carrier particle can be provided. Further, by using the composite oxide catalyst according to the present invention, the corresponding unsaturated acid or unsaturated nitrile can be produced form propane or isobutane at high yield.

BEST MODE FOR CARRYING OUT THE INVENTION

Hereinafter, the present invention will be described in detail. A composite oxide catalyst according to the present invention, which contains at least Mo, V and a component X (the component X being at least one element selected from among alkaline earth metal elements and rare earth elements), is carried by a carrier containing silica, in which the component X is uniformly distributed inside a catalyst particle. As a preferred embodiment of the composite oxide catalyst, an article as represented by the following general formula (1) is exemplified.

$$Mo_1V_aNb_bY_cX_dO_n \quad (1)$$

wherein a, b, c, d and n each represent an atomic ratio per Mo atom, in which a is in the range of $0.01 \leq a \leq 1$;
b is in the range of $0.01 \leq b \leq 1$;
c is in the range of $0.01 \leq c \leq 1$;
a/c as a ratio of a to c is in the range of $0<a/c<1$;
d is in the range of $0<d<1$; and
n is the number determined by an atomic valence of a component metal.

Further, as for atomic ratios: a to c per Mo atom, $0.1 \leq a \leq 0.4$, $0.01 \leq b \leq 0.2$ and $0.1 \leq c \leq 0.5$ are preferable, respectively.

d which is an atomic ratio of the component X per Mo atom is preferably in the range of $0<d<1$, more preferably in the range of $0.001 \leq d<0.1$ and, particularly preferably, $0.002 \leq d<0.01$. As for elements of the component X, Sr, Ba, Sc, Y (yttrium), La, Ce, Pr and Yb are preferable and Ce is particularly preferable.

c which is an atomic ratio of the component Y per Mo atom is preferably from $0.01 \leq c \leq 0.6$ and, more preferably, from $0.1 \leq c \leq 0.4$. As for elements of the component Y, Te and Sb are favorably used and Sb is industrially preferably used.

The composite oxide catalyst to be obtained by the production method according to the present invention is preferably a carried catalyst carried by a carrier containing silica as a main component. When the composite oxide catalyst is the catalyst carried by the carrier containing silica as a main component, since it has a high mechanical strength, it is favorably used in a vapor-phase catalytic oxidation reaction or a vapor-phase catalytic ammoxidation reaction using a fluidized bed reactor.

A content of silica in the carrier containing silica as a main component is, as $SiO_2$ equivalent, preferably from 20 to 60% by weight and, more preferably, from 25 to 55% by weight on the basis of an entire weight of a carried oxide catalyst containing an oxide of an element composing the catalyst and the carrier.

In the composite oxide catalyst according to the present invention, one of the particularly important points is that the component X is uniformly distributed in the catalyst particle. The term "uniformly" as used herein refers to a state in which distribution of the component X is not disproportionate in the catalyst particle. Preferably, the term "uniformly" refers to a state in which 80% or more (percentage by weight) of the oxide particles containing the component X are present in the catalyst particle as fine particles each having a particle diameter of 1 μm or less. When the term "uniformly" is favorably defined, it refers to a state in which a dispersion value (a value obtained by dividing a standard deviation by an average value) of a signal intensity ratio of the component X (the component X being at least one element selected from among alkaline earth metal elements and rate earth elements) to Si, at the time of composition analysis of a cross-section of the composite oxide catalyst particle, is in the range of 0 to 0.5. Further, the dispersion value is herein referred to as "$D_X$".

For the composition analysis, any one of ordinary composition analysis methods, for example, an SEM-EDX, an XPS, an SIMS and an EPMA can be used. The EPMA is favorably used thereamong. The term "EPMA" as used herein refers to a name commonly used for Electron Probe X-ray Microanalyzer (however, the term "X-Ray" may sometimes be omitted). This analyzer is an apparatus which can perform a composition analysis of a micro region (spot) by observing a characteristic X ray obtained by irradiating an accelerated electron beam on a substance. By using this EPMA, with regard to a cross-section of a solid particle such as a catalyst particle or a carrier particle, a concentration distribution of a specified element or information of a composition change can be obtained.

Further, in the present invention, the dispersion value ($D_X$) of the intensity ratio of the component X to Si according to the EPMA is measure-calculated on a cross-section of a particle to be measured in accordance with a technique of a face analysis by EPMA of a particle cross-section to be performed in the field of an ordinary catalyst in a manner as described below. Namely, firstly, distribution of an X-ray peak intensity (number of count: $I_{Si}$) of Si against a given position (x, y) of a catalyst particle cross-section is measured such that an entire area of the catalyst particle cross-section is covered. Next, distribution of an X-ray peak intensity (number of count: $I_X$) of the component X is measured in a same manner as in Si such that an entire area of the catalyst particle cross-section is covered. Based on a series of data (x, y, $I_{Si}$, $I_X$) obtained with regard to Si and the component X, a peak intensity ratio $I_R$ ($I_R=I_X/I_{Si}$) of the component X to Si at a same position (x,y) is obtained and, then, a simple mean value $(I_R)_{av}$ and a standard deviation S of $I_R$ are obtained and, subsequently, a value obtained by dividing the standard deviation S with the simple mean value $(I_R)_{av}$ is allowed to be the dispersion value ($D_X$). On this occasion, the simple mean value and the standard deviation may be obtained by ordinary methods.

Further, in order to prevent uncertainty of data by an edge effect of the particle cross-section in the above-described measurement, it is preferable that a region showing 10% of a cross-section in the catalyst particle cross-section, that is, a region corresponding to an outer peripheral portion of the particle is excluded and data on the remaining region showing 90% from a center in the catalyst particle cross-section is taken as an effective data and put for calculation. Of course, the above-described face analysis by the EPMA can be performed only on the inside of the catalyst particle cross-section in which a region corresponding to 10% of the outer peripheral portion of the particle is excluded from the beginning and, then, based on the thus-obtained data, the dispersion value $D_X$ can be determined in a same manner as in the above.

The face analysis of the catalyst particle cross-section may be performed in accordance with the technique which has been performed in the field of the ordinary catalyst as described above and is ordinarily favorably performed in a manner as described below.

Namely, firstly, the particle to be measured is buried in an appropriate matrix resin, ground as a whole until a cross-section of the thus-buried catalyst particle is exposed and, then, the EPMA measurement is performed on the catalyst particle having the thus-exposed cross-section as follows:

(1) a position of a sample is arranged such that a cross-section of the catalyst particle comes in a visual field of observation in the EPMA measurement; and (2) an electron beam is irradiated on the cross-section of the catalyst particle, an intensity of characteristic X ray of Si or the component X emitted from a portion on which the electron beam is irradiated is counted and, then, a face analysis is performed by scanning the region to be analyzed by the electron beam.

The composite oxide catalyst according to the present invention can be prepared by an ordinary method, for example, via the following three steps:

(I) a step of mixing raw materials;

(II) a step of drying the resultant raw material mixture obtained in step (I), to thereby obtain a catalyst precursor; and (III) a step of calcining the catalyst precursor obtained in step (II).

The term "mixing" as used herein means to dissolve or disperse raw materials which is catalyst-composing elements in an aqueous solvent.

The term "raw material" as used herein refers to an article to be used in step (I). At the time of preparing the composite oxide catalyst according to the present invention, a metallic raw material is not particularly limited and such compounds as described below can be used.

Namely, as for raw materials for Mo and V, ammonium heptamolybdate: $[(NH_4)_6Mo_7O_{24}.4H_2O]$ and ammonium metavanadate: $[NH_4VO_3]$ can favorably be used, respectively.

As for raw materials for Nb, niobic acid, an inorganic niobate and an organic niobate can be used. Particularly, niobic acid is favorable. Niobic acid is represented by $Nb_2O_5.nH_2O$ and is denoted also as niobium hydroxide or niobium hydrate. Further, a raw material solution in which a molar ratio of dicarboxylic acid/niobium is 1 to 4 is preferable. As for the dicarboxylic acid, oxalic acid is preferably used.

As for raw materials for Sb, antimony trioxide $[Sb_2O_3]$ is preferable.

As for raw materials for Te, telluric acid $[H_6TeO_6]$ is preferable.

As for raw materials for the component X, no material is particularly limited, so long as any of these elements is contained therein and compounds containing any of these elements and an article in which metal of any of these elements is solubilized by an appropriate reagent can be used. As for the compound containing any of these elements, ordinarily, a nitrate, a carboxylate, an ammonium salt of a carboxylic acid, an ammonium salt of a peroxocarboxylic acid, a halogenated ammonium salt, a halide, acetyl acetate, an alcoxide and the like can be used. Preferably, an aqueous raw material such as a nitrate, or a carboxylate can be used.

As for raw materials for silica, silica sol can be used. However, silica powder can be used either partially or entirely as the silica raw material. The silica powder is preferably that prepared by a high-temperature method. Further, the silica powder is more preferably dispersed in water and, then, used.

Hereinafter, preferred examples of preparation of catalysts according to the present invention consisting of steps (I) to (III) will be described.

(Step I: Step of Mixing Raw Materials)

An Mo compound, a V compound, an X component and, optionally, a component which becomes any one of other raw materials are added to water and, then, heated, to thereby prepare a mixture (A). On this occasion, an inside of a container may be in a nitrogen atmosphere. When Nb is allowed to be contained, an Nb compound and a dicarboxylic acid are added to water and, then, heated while mixing, to thereby prepare a mixture ($B_0$). Further, hydrogen peroxide may be added to the mixture ($B_0$), to thereby prepare a mixture (B). On this occasion, $H_2O_2/Nb$ (molar ratio) is preferably 0.5 to 20 and, particularly preferably from 1 to 10. Oxalic acid can further be added to either the mixture ($B_0$) or (B).

Depending on a composition to be targeted, the mixture (A), the mixture ($B_0$) or the mixture (B) is appropriately mixed, to thereby obtain a raw material mixture.

When the catalyst for ammoxidation according to the present invention is a silica-carrying catalyst, the raw material mixture is prepared such that it contains silica sol. Silica sol can appropriately be added thereto.

(Step II: Drying Step)

The raw material mixture obtained in step (I) is dried by a spray-drying method, to thereby obtain dry powder. For performing spraying in the spray-drying method, a centrifugal system, a two-fluid-nozzle system or a high-pressure nozzle system can be adopted. As for a heat source for drying, an air heated by steam, an electric heater or the like can be used. A temperature of a hot air at an inlet of a dryer is preferably from 150 to 300° C.

(Step III: Calcining Step)

An oxide catalyst can be obtained by calcining the dry powder obtained in the drying step. Calcining is performed at from 500 to 800° C. and, preferably, from 600 to 700° C. in an atmosphere of an inert gas, which is substantially free from oxygen, such as a nitrogen gas, an argon gas or a helium gas, preferably, while circulating the inert gas. A calcining period of time is from 0.5 to 20 hours and, preferably, from 1 to 8 hours.

The calcining can be performed by using a rotary kiln, a tunnel kiln, a tubular furnace, a fluidized calcining furnace or the like. The calcining can repeatedly be performed.

Before performing the calcining step, it is preferable that the dry powder is pre-calcined for from 1 to 5 hours at from 200 to 400° C. in an atmospheric environment or in a circulation of air.

In the presence of the oxide catalyst thus prepared, propane or isobutane is subjected to a vapor-phase catalytic oxidation or a vapor-phase catalytic ammoxidation reaction, to thereby prepare a corresponding unsaturated acid or an unsaturated nitrile.

Supply raw materials of propane or isobutane and ammonia are not necessarily highly pure but those of industrial grade can be used.

As for a supply oxygen source, air, air enriched with oxygen or pure oxygen can be used. Further, as a dilution gas, helium, argon, carbon dioxide, steam, nitrogen or the like may be supplied.

The vapor-phase catalytic oxidation of propane or isobutane can be performed under the following conditions:

a molar ratio of oxygen to be supplied for the reaction to propane or isobutane is from 0.1 to 6 and, preferably, from 0.5 to 4;

a reaction temperature is from 300 to 500° C. and, preferably, from 350 to 450° C.;

a reaction pressure is from $5\times10^4$ to $5\times10^5$ Pa and, preferably, from $1\times10^5$ to $3\times10^5$ Pa;

a contact period of time is from 0.1 to 10 (sec·g/cc) and, preferably, from 0.5 to 5 (sec·g/cc). In the present invention, the contact period of time can be determined by the following formula:

contact period of time (sec·g/cc)=$(W/F)\times273/(273+T)$ wherein W, F and T are defined as follows:

W=filled amount (g) of catalyst;

F=flow rate (Ncc/sec) of a raw material mixed gas under normal conditions (0° C., $1.013\times10^5$ Pa); and T=reaction temperature (° C.).

Vapor-phase catalytic ammoxidation of propane or isobutane can be performed under the following conditions:

a molar ratio of oxygen to be supplied for the reaction to propane or isobutane is from 0.1 to 6 and, preferably, from 0.5 to 4;

a molar ratio of ammonia to be supplied for the reaction to propane or isobutane is from 0.3 to 1.5 and, preferably, from 0.7 to 1.2;

a reaction temperature is from 350 to 500° C. and, preferably, from 380 to 470° C.;

a reaction pressure is from $5\times10^4$ to $5\times10^5$ Pa and, preferably, from $1\times10^5$ to $3\times10^5$ Pa; and a contact period of time is from 0.1 to 10 (sec·g/cc) and, preferably, from 0.5 to 5 (sec·g/cc).

As for a reaction method, any one of conventional methods such as a fixed bed method, a fluidized bed method and a moving bed method can be adopted and, due to easiness of removal of a reaction heat, the fluidized bed method is preferable thereamong.

Further, the reaction according to the present invention may either be a single current system or a recycle system.

EXAMPLE 1

Hereinafter, a composite oxide catalyst according to the present invention will be described with reference to embodiments of production of the catalyst and embodiment for production of acrylonitrile by a vapor-phase catalytic ammoxidation reaction, but the present invention is not limited thereto so long as it is within the purport thereof.

Performance of the ammoxidation reaction of propane is evaluated on the basis of the results of analyzing a reaction gas while taking a ratio of propane conversion and a ratio of selectivity of acrylonitrile as represented by the following formula as indicators:

(Ratio of propane conversion)=(Number of moles of reacted propane)/(Number of moles of supplied propane)×100

(Ratio of selectivity of acrylonitrile)=(Number of moles of produced acrylonitrile)/(Number of moles of reacted propane)×100  [Formula 1]

(Preparation of Aqueous Niobium Mixture)

In accordance with the specification according to JP 11-253801 A, an aqueous niobium mixture was prepared by a method as described below.

To 2552 g of water, 352 g of niobic acid containing 80% by weight of niobium in terms of $Nb_2O_5$ and 1344 g of oxalic acid dihydrate [$H_2C_2O_4\cdot2H_2O$] were added. A molar ratio of oxalic acid/niobium as feedstocks was 5.03 and a concentration of a feedstock niobium was 0.50 (mol-Nb/Kg-solution). The resultant solution was heated for one hour at 95° C. with stirring, to thereby obtain a mixture in which niobium is dissolved. This mixture was left standstill, cooled with ice, subjected to a suction filtration for removing a solid content, to thereby obtain a uniform aqueous niobium mixture. The molar ratio of the oxalic acid/niobium of this aqueous niobium mixture was found to be 2.52 by the analysis described below.

10 g of this aqueous niobium mixture was precisely weighed and put in a crucible, dried for a night at 95° C. and subjected to a heat treatment for one hour at 600° C., to thereby obtain 0.8228 g of $Nb_2O_5$. From this result, it was found that the niobium concentration was 0.618 (mol-Nb/Kg-solution).

3 g of this aqueous niobium mixture was precisely weighed and put in a glass beaker having a capacity of 300 ml, added with about 200 ml of hot water having a temperature of about 80° C. and, then, added with 10 ml of a 1:1 sulfuric acid. The resultant mixture was titrated by using a ¼ N $KMnO_4$ solution with stirring while being kept at a temperature of 70° C. on a hot stirrer. A point at which a faint light pink color lasted for about 30 seconds or more was defined as an end-point. A concentration of oxalic acid was determined on the basis of the resultant titer in accordance with the following formula and, as a result, it was 1.558 (mol-oxalic acid/Kg):

$2KMnO_4+3H_2SO_4+5H_2C_2O_4 \rightarrow K_2SO_4+2MnSO_4+$ 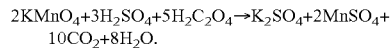
$10CO_2+8H_2O$.

The thus-obtained aqueous niobium mixture was used as the aqueous niobium mixture ($B_0$) for use in preparation of a catalyst to be described below.

EXAMPLE 1

(Preparation of Catalyst)

An oxide catalyst in which a feedstock composition formula is represented by $Mo_1V_{0.21}Nb_{0.09}Sb_{0.25}Ce_{0.005}O_n/45.0$ wt%-$SiO_2$ was produced as follows:

To 4584 g of water, 915.0 g of ammonium heptamolybdate $[(NH_4)_6Mo_7O_{24}\cdot 4H_2O]$, 127.3 g of ammonium metavanadate $[NH_4VO_3]$, 188.8 g of diantimony trioxide $[Sb_2O_3]$ and 11.25 g of cerium nitrate·hexahydrate $[Ce(NO_3)_3\cdot 6H_2O]$ were added and heated for 2.5 hours at 90° C. with stirring, to thereby obtain a mixture A-1.

To 754.6 g of the aqueous niobium mixture ($B_0$), 105.8 g of hydrogen peroxide solution containing 30% by weight of $H_2O_2$ was added and mixed for 10 minutes at room temperature, to thereby prepare a mixture B-1.

After the thus-obtained mixture A-1 was cooled to 70° C., 2980 g of silica sol containing 30.2% by weight of $SiO_2$ was added thereto and, further, 220.4 g of hydrogen peroxide solution containing 30% by weight of $H_2O_2$ was added thereto and, then, the resultant mixture was continuously stirred for one hour at 50° C. Next, to the resultant mixture, the mixture B-1 was added, to thereby obtain a raw material mixture.

The thus-obtained raw material mixture was supplied to a centrifugal spray dryer and dried, to thereby obtain dry powder in a minute sphere state. It was found that temperatures at an inlet and an outlet of the dryer were 210° C. and 120° C., respectively.

480 g of the thus-obtained dry powder was filled in a calcining tube made of stainless steel having a diameter of 3 inches and, then, calcined for 2 hours at 640° C. in a flow of a nitrogen gas at a rate of 5.0 NL/min while the tube was rotated, to thereby obtain a catalyst.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 μm; and spot diameter: 1.0 μm. As a dispersible crystal at the time of Si measurement, LiF (lithium fluoride) (200 face being used) was used. At the time of measurement of Ce, PET (polyethylene terephthalate) (002 face being used) was used. As for a detector, a Kr-Exatron detector (proportional counter tube) was used. The results are shown in Table 1.

(Ammoxidation Reaction of Propane)

35 g of the thus-obtained catalyst was filled in a Vycor glass fluidized-bed reaction tube having an inner diameter of 25 mm. A gaseous mixture having a molar ratio of propane:ammonia:oxygen:helium of 1:1:3:18 was fed into the reaction tube at a rate of contact period of time of 2.8 (sec·g/cc) with a reaction temperature of 440° C. under atmospheric pressure as a reaction pressure. The results obtained 5 hours after the start-up of the reaction are shown in Table 1, while the results obtained 1200 hours and 2400 hours after are shown in Table 2.

COMPARATIVE EXAMPLE 1

(Preparation of Catalyst)

An oxide catalyst in which a feedstock composition formula is represented by $Mo_1V_{0.21}Nb_{0.09}Sb_{0.25}Ce_{0.0005}O_n/45.0$ wt%-$SiO_2$ was prepared as follows:

To 4602 g of water, 918.5 g of ammonium heptamolybdate $[(NH_4)_6Mo_7O_{24}\cdot 4H_2O]$, 127.8 g of ammonium metavanadate $[NH_4VO_3]$, 189.6 g of diantimony trioxide $[Sb_2O_3]$ and 4.46 g of cerium hydroxide $[Ce(OH)_4]$ were added and heated for 2.5 hours at 90° C. with stirring, to thereby obtain a mixture A-2. To 757.5 g of the aqueous niobium mixture (B0), 106.2 g of hydrogen peroxide solution containing 30% by weight of $H_2O_2$ was added and mixed for 10 minutes at room temperature, to thereby prepare a mixture B-2.

After the thus-obtained mixture A-2 was cooled to 70° C., 2980 g of silica sol containing 30.2% by weight of $SiO_2$ was added thereto. Next, to the resultant mixture, the mixture B-2 was added, to thereby obtain a raw material mixture.

The thus-obtained raw material mixture was supplied to a centrifugal spray dryer and dried, to thereby obtain dry powder in a minute sphere state. It was found that temperatures at an inlet and an outlet of the dryer were 210° C. and 120° C., respectively.

480 g of the thus-obtained dry powder was filled in a calcining tube made of stainless steel having a diameter of 3 inches and, then, calcined for 2 hours at 640° C. in a flow of a nitrogen gas at a rate of 5.0 NL/min while the tube was rotated, to thereby obtain a catalyst.

(Composition Analysis)

An EMPA measurement was performed on the thus-obtained oxide catalyst in a same manner as in Example 1. The results are shown in Table 1.

(Ammoxidation Reaction of Propane)

35 g of the thus-obtained catalyst was filled in a Vycor glass fluidized-bed reaction tube having an inner diameter of 25 mm. A gaseous mixture having a molar ratio of propane:ammonia:oxygen:helium of 1:1:3:18 was fed into the reaction tube at a rate of contact period of time of 2.8 (sec·g/cc) with a reaction temperature of 440° C. under atmospheric pressure as a reaction pressure. The results obtained 5 hours after the start-up of the reaction are shown in Table 1, while the results obtained 1200 hours and 2400 hours after are shown in Table 2.

COMPARATIVE EXAMPLE 2

(Preparation of Catalyst)

An oxide catalyst in which a feedstock composition formula is represented by $Mo_1V_{0.21}Nb_{0.09}Sb_{0.25}Ce_{0.05}O_n/45.0$ wt%-$SiO_2$ was prepared as follows. The same preparation procedure as in Example 1 was repeated except that 44.6 g of cerium hydroxide $[Ce(OH)_4]$ was added as a cerium raw material.

(Composition Analysis)

An EMPA measurement was performed on the thus-obtained oxide catalyst in a same manner as in Example 1. The results are shown in Table 1.

(Ammoxidation Reaction of Propane)

An ammoxidation reaction of propane was performed against the thus-obtained oxide catalyst in a same manner as in Example 1. The results obtained 5 hours after the start-up of the reaction are shown in Table 1, while the results obtained 1200 hours and 2400 hours after are shown in Table 2.

EXAMPLE 2

(Preparation of Catalyst)

An oxide catalyst in which a feedstock composition formula is represented by $Mo_1V_{0.21}Nb_{0.09}Sb_{0.25}Ce_{0.0005}O_n/45.0$ wt%-$SiO_2$ was prepared as follows. To 4584 g of water, 915.0 g of ammonium heptamolybdate $[(NH_4)_6Mo_7O_{24}\cdot 4H_2O]$, 127.3 g of ammonium metavanadate $[NH_4VO_3]$, 188.8 g of diantimony trioxide $[Sb_2O_3]$ and 11.25 g of cerium nitrate hexahydrate $[Ce(NO_3)_3\cdot 6H_2O]$ were added and heated for 2.5 hours at 90° C. with stirring, to thereby obtain a mixture A-4.

To 754.6 g of the aqueous niobium mixture (B0), 105.8 g of hydrogen peroxide solution containing 30% by weight of $H_2O_2$ was added and mixed for 10 minutes at room temperature, to thereby prepare a mixture B-4.

After the thus-obtained mixture A-4 was cooled to 70° C., 1490 g of silica sol containing 30.2% by weight of $SiO_2$ was added thereto and, further, 220.4 g of hydrogen peroxide solution containing 30% by weight of $H_2O_2$ was added thereto and, then, continuously stirred for one hour at 50° C. Next, to the resultant mixture, the mixture B-4 and a dispersion in which 450 g of powder silica was dispersed in 6300 g of water were added in the stated order, to thereby obtain a raw material mixture.

The thus-obtained raw material mixture was supplied to a centrifugal spray dryer and dried, to thereby obtain dry powder in a minute sphere state. It was found that temperatures at an inlet and an outlet of the dryer were 210° C. and 120° C., respectively.

480 g of the thus-obtained dry powder was filled in a calcining tube made of stainless steel having a diameter of 3 inches and, then, calcined for 2 hours at 640° C. in a flow of a nitrogen gas at a rate of 5.0 NL/min while the tube was rotated, to thereby obtain a catalyst.

(Composition Analysis)

An EMPA measurement was performed on the thus-obtained oxide catalyst in a same manner as in Example 1. The results are shown in Table 1.

(Ammoxidation Reaction of Propane)

35 g of the thus-obtained catalyst was filled in a Vycor glass fluidized-bed reaction tube having an inner diameter of 25 mm. A gaseous mixture having a molar ratio of propane:ammonia:oxygen:helium of 1:1:3:18 was fed into the reaction tube at a rate of contact period of time of 2.8 (sec·g/cc) with a reaction temperature of 440° C. under atmospheric pressure as a reaction pressure. The results are shown in Table 1.

EXAMPLE 3

(Preparation of Catalyst)

An oxide catalyst in which a feedstock composition formula is represented by $Mo_1V_{0.21}Nb_{0.09}Sb_{0.25}Sc_{0.005}O_n/45.0$ wt %-$SiO_2$ was prepared as follows. The same preparation procedure as in Example 2 was repeated except that 7.85 g of scandium nitrate tetrahydrate [$Sc(NO_3)_3 \cdot 4H_2O$] was added in place of cerium nitrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and Sc measurements, LiF (lithium fluoride) (200 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results are shown in Table 1.

EXAMPLE 4

(Preparation of Catalyst)

An oxide catalyst in which a feedstock composition formula is represented by $Mo_1V_{0.21}Nb_{0.09}Sb_{0.25}Y_{0.005}O_n/45.0$ wt %-$SiO_2$ was prepared as follows. The same preparation procedure as in Example 2 was repeated except that 9.92 g of yttrium nitrate hexahydrate [$Y(NO_3)_3 \cdot 6H_2O$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si measurement, LiF (lithium fluoride) (200 face being used) was used. At the time of Y measurement, PET (polyethylene terephthalate) (002 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results obtained 5 hours after the start-up of the reaction are shown in Table 1, while the results obtained 1200 hours and 2400 hours after are shown in Table 2.

EXAMPLE 5

(Preparation of Catalyst)

An oxide catalyst in which a feedstock composition formula is represented by $Mo_1V_{0.21}Nb_{0.09}Sb_{0.25}La_{0.005}O_n/45.0$ wt %-$SiO_2$ was prepared as follows. The same preparation procedure as in Example 2 was repeated except that 11.21 g of lanthanum nitrate hexahydrate [$La(NO_3)_3 \cdot 6H_2O$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and La measurements, LiF (lithium fluoride) (200 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results are shown in Table 1.

EXAMPLE 6

(Preparation of Catalyst)

An oxide catalyst in which a feedstock composition formula is represented by $Mo_1V_{0.21}Nb_{0.09}Sb_{0.25}Pr_{0.005}O_n/45.0$ wt %-$SiO_2$ was prepared as follows. The same preparation procedure as in Example 2 was repeated except that 11.27 g of praseodymium nitrate hexahydrate [$Pr(NO_3)_3 \cdot 6H_2O$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and Pr measurements, LiF (lithium fluoride) (200 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results are shown in Table 1.

EXAMPLE 7

(Preparation of Catalyst)

An oxide catalyst in which a feedstock composition formula is represented by $Mo_1V_{0.21}Nb_{0.09}Sb_{0.25}Yb_{0.005}O_n/45.0$ wt %-$SiO_2$ was prepared as follows. The same preparation procedure as in Example 2 was repeated except that 10.70 g of ytterbium nitrate trihydrate [$Yb(NO_3)_3 \cdot 3H_2O$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and Yb measurements, LiF (lithium fluoride) (200 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results are shown in Table 1.

EXAMPLE 8

(Preparation of Catalyst)

An oxide catalyst in which a feedstock composition formula is represented by $Mo_1V_{0.21}Nb_{0.09}Sb_{0.25}Sr_{0.005}O_n/45.0$ wt %-$SiO_2$ was prepared as follows. The same preparation procedure as in Example 2 was repeated except that 5.48 g of strontium nitrate [$Sr(NO_3)_2$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and Sr measurements, LiF (lithium fluoride) (200 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results are shown in Table 1.

EXAMPLE 9

(Preparation of Catalyst)

An oxide catalyst in which a feedstock composition formula is represented by $Mo_1V_{0.21}Nb_{0.09}Sb_{0.25}Ba_{0.005}O_n/45.0$ wt %-$SiO_2$ was prepared as follows. The same preparation procedure as in Example 2 was repeated except that 6.77 g of barium nitrate [$Ba(NO_3)_2$] was added in place of cerium nitrate hexahydrate.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si and Ba measurements, LiF (lithium fluoride) (200 face being used) was used. As for a detector, a Kr-Exatron detector (proportional counter tube) was used. The results are shown in Table 1.

(Ammoxidation reaction of Propane)

An ammoxidation reaction of propane was performed against the thus-obtained oxide catalyst in a same manner as in Example 1. The results obtained 5 hours after the start-up of the reaction are shown in Table 1, while the results obtained 1200 hours and 2400 hours after are shown in Table 2.

COMPARATIVE EXAMPLE 3

(Preparation of Catalyst)

An oxide catalyst in which a feedstock composition formula is represented by $Mo_1V_{0.21}Nb_{0.09}Sb_{0.25}Ce_{0.05}O_n/45.0$ wt %-$SiO_2$ was prepared as follows.

The same preparation procedure as in Example 2 was repeated except that the weight of cerium nitrate hexahydrate thus added was changed from 11.25 g to 112.5 g.

(Composition Analysis)

An EPMA measurement was performed on the thus-obtained oxide catalyst by using an EPMA 1600 available from Shimadzu Corporation. Measuring conditions are as follows: accelerating voltage: 0 to 30 kV; step width: 1.0 µm; and spot diameter: 1.0 µm. As a dispersible crystal at the time of Si measurement, LiF (lithium fluoride) (200 face being used) was used. At the time of measurement of Ce, PET (polyethylene terephthalate) (002 face being used) was used. As for a detector, a Kr-Exatron detector (proportional counter tube) was used. The results are shown in Table 1.

(Ammoxidation Reaction of Propane)

An ammoxidation reaction of propane was performed against the thus-obtained oxide catalyst in a same manner as in Example 1. The results obtained 5 hours after the start-up of the reaction are shown in Table 1, while the results obtained 1200 hours and 2400 hours after are shown in Table 2.

TABLE 1

| | X component raw material | Dispersion value | AN yield after 5 hours (%) |
|---|---|---|---|
| Example 1 | Cerium nitrate hexahydrate | 0.15 | 53.8 |
| Comparative Example 1 | Cerium hydroxide | 0.81 | 49.5 |
| Comparative Example 2 | Cerium hydroxide | 0.95 | 49.8 |
| Example 2 | Cerium nitrate hexahydrate | 0.13 | 54.3 |
| Example 3 | Scandium nitrate tetrahydrate | 0.14 | 53.1 |
| Example 4 | Yttrium nitrate hexahydrate | 0.16 | 52.9 |
| Example 5 | Lanthanide nitrate hexahydrate | 0.16 | 52.8 |
| Example 6 | Praseodymium nitrate hexahydrate | 0.12 | 53.6 |
| Example 7 | Ytterbium nitrate trihydrate | 0.13 | 53.5 |
| Example 8 | Strontium nitrate | 0.15 | 52.4 |
| Example 9 | Barium nitrate | 0.16 | 52.5 |
| Comparative Example 3 | Cerium nitrate hexahydrate | 0.44 | 50.3 |

TABLE 2

|  | AN yield after 1200 hours (%) | AN yield after 2400 hours (%) |
|---|---|---|
| Example 1 | 53.5 | 53.1 |
| Comparative Example 1 | 35.0 | 32.5 |
| Example 4 | 54.1 | 53.9 |
| Example 9 | 52.2 | 51.8 |
| Comparative Example 3 | 47.1 | 45.2 |

While the present invention has been described in detail and with reference to specific embodiments thereof, it will be apparent to one skilled in the art that various changes and modifications can be made therein without departing from the spirit and scope thereof.

The present application is based on Japanese Patent Application No. 2004-236956 filed on Aug. 17, 2004 and Japanese Patent Application No. 2004-236957 filed on Aug. 17, 2004, and the contents thereof are incorporated herein by reference.

INDUSTRIAL APPLICABILITY

Therefore, the complex oxide catalyst according to the present invention can usefully be applied in an industrial production process for producing a corresponding unsaturated acid or a corresponding unsaturated nitrile by subjecting propane or isobutane to a vapor-phase catalytic oxidation reaction or a vapor-phase catalytic ammoxidation reaction.

The invention claimed is:

1. A vapor-phase catalytic oxidation reaction or a vapor-phase catalytic ammoxidation reaction of propane or isobutane with a composite oxide catalyst, wherein said composite oxide catalyst comprises a catalyst particle of the following formula (1) and a carrier containing silica, $$Mo_1V_aNb_bY_cX_dO_n \qquad (1)$$

wherein a, b, c, d and n each represent an atomic ratio per Mo atom, in which
a is in the range of $0.01 \leq a \leq 1$;
b is in the range of $0.01 \leq b \leq 1$;
c is in the range of $0.01 \leq c \leq 1$;
a/c as a ratio of a to c is in the range of $0 < a/c < 1$;
d is in the range of $0.002 \leq d < 0.01$; and
n is the number determined by an atomic valence of a component metal;
X is at least one selected from the group consisting of Sr, Ba, Sc, yttrium, La, Ce, Pr and Yb; and
Y is at least one selected from the group consisting of Te and Sb:
wherein the composite oxide catalyst is carried by the carrier,
wherein the component X is uniformly distributed in the catalyst particle, and
wherein a dispersion value $D_X$ of a signal intensity ratio as measured by EPMA of the component X to Si, at the time of composition analysis of a cross-section of the catalyst particle, is $0 < D_X < 0.5$:
wherein said composite oxide catalyst is prepared in a method comprising,
mixing a silica and an Nb compound into a mixture containing an Mo compound, a V compound, a Y compound and an X compound to prepare a raw material mixture,
spray-drying the raw material mixture to prepare a dry powder, and calcining the dry powder:

wherein the vapor-phase catalytic oxidation reaction or the vapor-phase catalytic ammoxidation reaction of propane or isobutane comprises a step of contacting said composite oxide catalyst with propane or isobutane.

2. The method according to claim 1, which is a vapor-phase catalytic oxidation of propane or isobutane with the composite oxide catalyst to prepare an unsaturated acid.

3. The method according to claim 1, which is a vapor-phase catalytic ammoxidation of propane or isobutane to prepare an unsaturated nitrile.

4. A method for producing a composite oxide catalyst comprising a catalyst particle of the following formula (1) and a carrier containing silica, $$Mo_1V_aNb_bY_cX_dO_n \qquad (1)$$

wherein a, b, c, d and n each represent an atomic ratio per Mo atom, in which
a is in the range of $0.01 \leq a \leq 1$;
b is in the range of $0.01 \leq b \leq 1$;
c is in the range of $0.01 \leq c \leq 1$;
a/c as a ratio of a to c is in the range of $0 < a/c < 1$;
d is in the range of $0.002 \leq d < 0.01$; and
n is the number determined by an atomic valence of a component metal;
X is at least one selected from the group consisting of Sr, Ba, Sc, yttrium, La, Ce, Pr and Yb; and
Y is at least one selected from the group consisting of Te and Sb:
wherein the composite oxide catalyst is carried by the carrier,
wherein the component X is uniformly distributed in the catalyst particle, and
wherein a dispersion value $D_X$ of a signal intensity ratio as measured by EPMA of the component X to Si, at the time of composition analysis of a cross-section of the catalyst particle, is $0 < D_X < 0.5$:
said method comprising,
mixing a silica and an Nb compound into a mixture containing an Mo compound, a V compound, a Y compound and an X compound to prepare a raw material mixture,
spray-drying the raw material mixture to prepare a dry powder, and calcining the dry powder.

5. The method according to claim 4,
wherein the component X is at least one element selected from Sc, Y (yttrium), La, Ce, Pr and Yb.

6. The method according to claim 4,
wherein the composite oxide catalyst is carried by 20 to 60% by weight of silica as $SiO_2$ equivalent.

7. The method according to claim 4,
wherein 80 wt % or more of oxide particles containing the component X are present in the catalyst particle as particles each having a particle diameter of 1 μm or less.

8. The method according to claim 4,
wherein the atomic ratios of a to c per Mo atom are $0.1 \leq a \leq 0.4$, $0.01 \leq b \leq 0.2$ and $0.1 \leq c \leq 0.5$.

9. The method according to claim 4,
wherein X is Ce and Y is Sb.

10. The method according to claim 4,
wherein the c which is an atomic ratio of the component Y per Mo atom is $0.01 \leq c \leq 0.6$.

* * * * *